United States Patent
Bitensky et al.

(12)

(10) Patent No.: US 6,506,381 B1
(45) Date of Patent: Jan. 14, 2003

(54) MODIFIED RED BLOOD CELL THAT HAS SURFACE MOLECULES THAT NEUTRALIZE CHEMICAL AGENTS

(75) Inventors: Mark W. Bitensky, Waban, MA (US); Tatsuro Yoshida, Newton, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 09/609,482

(22) Filed: Jul. 5, 2000

Related U.S. Application Data

(63) Continuation of application No. PCT/US99/00216, filed on Jan. 6, 1999
(60) Provisional application No. 60/070,577, filed on Jan. 6, 1998.

(51) Int. Cl.[7] ................................................ A01N 63/00
(52) U.S. Cl. ........................................ 424/93.73; 435/2
(58) Field of Search ............................ 435/2; 424/93.73

(56) References Cited

PUBLICATIONS

Nussbaum et al., "Membrane–Bound Antiviral Antibodies as Receptors for Sendai Virions in Receptor–Depleted Erythrocytes", Virology 138 : 185–197 (1984).*

* cited by examiner

*Primary Examiner*—Sandra E. Saucier
(74) *Attorney, Agent, or Firm*—Kevin M. Farrell

(57) ABSTRACT

Disclosed are modified red blood cells which function as deployment platforms for important biomolecules. Such modified red blood cells can confer, for example, in vivo protection against exposure to an otherwise lethal nerve agent.

7 Claims, No Drawings

MODIFIED RED BLOOD CELL THAT HAS SURFACE MOLECULES THAT NEUTRALIZE CHEMICAL AGENTS

This application claims Benefit under 35 U.S.C. 365(a) of PCT/US99/00216 filed Jan. 6, 1999 which claims Benefit of Provisional 60/070577 Jan. 6, 1998.

GOVERNMENT SUPPORT

This invention was made with Government Support under Contract Number MDA972-96-K-0002 awarded by DARPA. The Government has certain rights in the invention.

BACKGROUND OF THE INVENTION

The red blood cell is a dominant presence in the circulatory system, representing approximately 98% of the formed elements which are present. Therefore, these cells can be viewed as a potentially important deployment platform for a variety of biomolecules which can be attached and displayed on the surface of the red blood cells. Barriers to some forms of such a deployment strategy include, for example, the fact that such modified red blood cells may be short-lived in circulation, thereby rendering them less effective. A strategy for the successful development of a red blood cell platform could provide a means for the treatment/and or prevention of a wide range of human disorders.

SUMMARY OF THE INVENTION

The present invention relates to modified red blood cells which function as deployment platforms for important biomolecules. Such modified red blood cells can confer, for example, in vivo protection against exposure to an otherwise lethal nerve agent.

DETAILED DESCRIPTION OF THE INVENTION

The present invention is based on the discovery that red blood cells, modified as described herein, can function as a successful deployment platform for important biomolecules. More specifically, as discussed in the Exemplification section which follows, Applicant has demonstrated in vivo protection against exposure of an animal to an otherwise lethal nerve agent. Protection was provided by decorating red blood cells in the animal with an enzyme capable of degrading the nerve agent.

Thus, the present invention relates, in one aspect, to a modified red blood cell which is relatively long-lived in circulation, the modified red blood cell bearing on its surface at least one biomolecule capable of neutralizing challenge by an endogenous or exogenous agent. As used herein, the expression "long-lived in circulation" will be defined within the context of ex vivo modification and reintroduction. That is, when red blood cells are removed from an animal, modified ex vivo and reintroduced into the animal, the long-lived criteria is satisfied when at least about 70% remain in circulation 24 hours after reintroduction.

The expression "biomolecule", as used herein, refers to any molecule which may be found in a living organism. With respect to the present invention, proteins are the most significant class of biomolecules. However, other important classes of biomolecules are included within the scope of the present invention, including, for example, carbohydrates. In general, the role of the biomolecule on the surface of the red blood cell is to either 1) act as an affinity reagent, specifically binding to another biomolecule; or 2) act as a molecular tool, modifying or degrading a biomolecule of interest.

As mentioned above, the proteins are a particularly significant class of biomolecules. The proteins include such important species as antibodies (which are useful as affinity reagents) and enzymes (which can catalyze the modification or degradation of a biomolecule of interest).

As used herein, the expression "endogenous" refers to agents (e.g., chemical or biological agents) which are typically found in the animal of interest. The expression "exogenous" refers to agents which are not typically found in the organism of interest. Issues to be considered in connection with the neutralization of endogenous versus exogenous agents using a biomolecule fixed to a red blood cell platform are not necessarily identical. The experiments described in the Exemplification section which follows relate specifically to an exogenous chemical agent.

Modified red blood cells of the type described herein are capable of neutralizing challenge by an endogenous or exogenous agent. The expression "neutralizing challenge" can not be defined precisely for all endogenous or exogenous agents. Rather, one must consider each endogenous or exogenous agent on a case by case basis, and consider the consequences of exposure or challenge by such agents to determine the meaning of the term "neutralizing".

Consider, for example, exogenous biological agents such as bacteria or viruses. Certain pathologies are associated with bacterial or viral infection—such pathologies can be determined by reference to medical handbooks. "Neutralization", as used herein, can refer, for example, to the prevention, elimination, mitigation, or delay in onset of such pathologies.

In the Exemplification section set forth below, an exogenous chemical agent is considered. More specifically, a toxic nerve agent is introduced into an animal carrying modified red blood cells of the present invention. In the absence of the modified red blood cells, animals exposed to the nerve agent die. Thus, in this context, "neutralization" refers to the fact that animals carrying the modified red blood cells survive.

An example which relates to an endogenous agent is LDL cholesterol. It is known that LDL cholesterol is found in vivo in both oxidized and reduced states. It is the oxidized form of LDL cholesterol that is dangerous. It is ingested by the cells of an atherosclerotic plaque which swell causing occlusion. Certain individuals apparently underexpress the enzyme responsible for maintaining LDL cholesterol in the reduced form (glutathione peroxidase). A method of therapy in such individuals is to deploy this enzyme on the surface of red blood cells thereby aiding in the maintenance of LDL cholesterol in the reduced form.

In another aspect, the present invention relates to a modified red blood cell, the surface of which is decorated with an ensemble (i.e., a plurality) of biomolecules. Such an ensemble of molecules can work in concert to achieve a desired neutralizing effect. The use of an ensemble of biomolecules is particularly important with respect to the neutralization of complex exogenous biological agents such as bacteria and viruses.

For example, red blood cells can be modified to bear an antibody or antibodies specific for a bacterium of interest. Such antibodies can bring the modified red blood cell into contact with the bacterium of interest if present in the circulation system. Other biomolecules present on the surface of the red blood cell can be provided which have the ability to breach the outer membrane/cell wall of the bacterium. These include, for example, lysozymes, bacteriocidal permeability increasing peptides and other pore forming antimicrobials. In addition, the bacterial electron transport array may be used to generate hydroxyl radicals within the bacterial inner cell membrane. Electron mediators such as hemin, derivatives of quinones, menadione or methyl viologen may be deployed on the surface of the red blood cell. Such electron mediators will produce hydroxyl radicals within the bacterial inner membrane by reducing oxygen directly. The penetration of such electron mediators will be assisted by the presence of lysozyme, which removes the peptidoglycan and allows the interaction of the electron mediator with the inner membrane. Potential synergy with bacteriocidal permeability increasing peptides for further disruption of lipo-polysaccharide or peptidoglycan layers is also likely.

The killing of bacteria by the addition of hemin has been demonstrated in relevant experiments. More specifically, this has been demonstrated in *B. subtilis* as well as *S. aureus* and other gram positive bacteria. Oxygen was required for bacterial killing. Bacteriocidal quantities of hemin did not damage bacteria in the absence of oxygen. Porphyrin without iron was also tested and a lack of bacteriocidal effect was observed due to the essential role of Fe in electron mediation. Moreover, when Zn was substituted for Fe the resulting complex demonstrated the expected reduction in bacteriocidal efficacy. It was also demonstrated that hemin, attached to polyethylene glycol tethers, does not kill bacteria with an intact peptidoglycan coat. The killing of gram negatives was achieved with hemin, provided that the lipopolysaccharide layer was first disrupted with polyethylene imine.

Deploying and ordering the bioengineered macromolecules into a multicomponent array yields large functional dividends. It can readily be demonstrated that a progression from unconnected to connected and ordered elements leads to increasing efficacy. This can be demonstrated through the production of random attachments to red cells followed by a progression to specific ordered attachments. The savings in diffusion time and gains in substrate concentrations that arise from ordering such a system are significant. Two principal technologies exist: a sequential methodology (such as is required for the use of most linkage strategies such as avidin-biotin and solid phase peptide synthesis) and a massively parallel, simultaneously self-assembling system (such as is possible with coded PNA constructions). The self-assembling PNA constructs will reliably preserve the topology that has been initially designed into the array. The PNA strategies offer an advantage in that mild reaction conditions are required, high affinity and high specific binding is achieved and a virtually unlimited library of complementary sequences are available.

More generally, biomolecules can be attached to the surface of red blood cells in vitro using any appropriate chemical functionality. For example, PNAs linked to an activated carboxylic acid moiety via a primary amino group represents one approach. Alternatively, attachment of an avidin anchor on biotinylated red blood cells can be used to attach a biotinylated enzyme. The attachment of a biotin anchor on a red blood cell attached to an enzyme to which avidin has been linked is also an option. Finally, the use of tannin to anchor avidin to the red blood cell platform for subsequent attachment of a biotinylated enzyme is also a viable option.

To create an optimal, stable foundation for the biomolecule ensemble, it may be necessary to introduce sites on biomolecules which facilitate attachment to red blood cells. Chemical modification of natural proteins is inexpensive and technically simple, but rarely permits site- and quantity-controlled reactions. Moreover, it never allows construction at a specified position on the protein surface that has been chosen by such criteria as orientation with respect to the substrate or to other components of the ensemble. Alternatively, standard recombinant technology permits the facile engineering of special properties at specific sites. These properties may be expressed by amino acid residues with unusual chemistry, such as cysteine, cassettes that encode specific, high-affinity binding domains, such as that for biotin, or sequences that direct specific enzymatic modification such as fatty acid conjugation.

Additional advantage can be gained by introducing attachment sites on biomolecules. These sites allow the ensemble components to be readily assembled into ordered arrays. The description in the preceding paragraph applies to sites required for the attachment of components to the red blood cell surface. With a complex, highly organized ensemble comes the need to engineer into a given component more than one site, each having its own special chemistry.

The chemistries for attaching PNA to these sites could have commonalities, but site selection for PNA attachment would have to be made on an enzyme-specific basis. Minor imprecision is tolerable if the process of self-assembly severely limits the incorporation of "incorrectly" modified components.

Using techniques such as those described above, 5,000 to 10,000 alkaline phosphatase molecules have been attached to various human and animal model red blood cells. The morphology, in vitro biophysical diagnostics and in vivo persistence studies have been carried out. Avidin has been modified to add carbohydrate moieties to reduce undesirable hydrophobic interactions on the avidin surface. A specific panel of in vitro biophysical diagnostic tests for the prediction of human red cell survival in vivo have been developed. Advanced nano-fabricated arrays which simulate the properties of in vivo capillary channels have been developed in order to evaluate the biophysical properties of decorated cells. Biochemical methods have been developed in the form of sialic acid attachments for rendering enzymatic decorations invisible to the clotting and immune systems.

Enhanced catalysis and enhanced enzyme stability are also issues relevant to red cell deployment. Gains in specificity and efficiency over those exhibited by wild-type enzymes may greatly improve the effectiveness of the deployment system. Methods of library construction via mutagenesis and phage display are well-known in the art. To identify an enzyme having enhanced activity it is first necessary to establish an efficient screening method. Improvement in specificity is a qualitative issue and may require the synthesis of special substrates for use in connection with ELISA or other high throughput assay systems. Improvement in efficiency is quantitative and the assay must be simple and precise.

To enhance enzyme stability without following the experimental route outlined in the preceding paragraph, it may be useful to screen high-temperature microbes for a more stable version of an enzyme of interest. It may also be demonstrated that the incorporation of a marginally stable enzyme into a well-ordered ensemble will confer a microenvironment which enhances stability.

Another advance in the implementation process is represented in the development of a new process for storing red blood cells which yields excellent levels of recovery with in vivo 24 hour post-transfusion measurements after 9 weeks of storage.

In another aspect, the present invention relates to a method for occluding the capillaries that feed inflammation and neoplastic processes, thereby eliminating, or reducing, associated pathologies. It is known that tumors and inflammatory processes induce the formation of new capillary vessels which provide perfusion. These newly formed vessels are enriched in cell-adhesion molecules, relative to their pre-existing counterparts in the body. By deploying red blood cells bearing biomolecules which specifically bind to cell adhesion molecules, it is possible to specifically occlude the vessels which perfuse tumors or inflammatory processes.

In addition to the ex vivo modification of red blood cells, in vivo modification is also possible. This would entail initial infusion of anchoring molecules which primarily insert into red cells. A secondary infusion would set into place the designated biomolecular tool.

EXEMPLIFICATION i) Biotinylation Procedure

Fresh rat blood was obtained through either cardiac puncture or venipuncture of the subclavian vein. The cells were suspended to Hct 10 in TEA buffer (50 mM triethanolamine, 100 mM $NaC_1$, 10 mM glucose, 2 mM $MgCl_2$, adjusted to pH 7.9). NHS-biotin (Pierce catalog #21217) solution (1 mg/ml in 140 mM NaCl) was prepared. Cells were added to 0.03 mg/ml final concentration. The suspended cells were then incubated at room temperature for 30 minutes on a Nutator.

Following incubation, the cells were washed once in ALP (128 mM NaCl, 10 mM glucose, 10 mM Na HEPES, 1 mM $CaCl_2$, 0.5 mM $MgCl_2$, adjusted to pH 7.4) buffer with 10 mg/ml bovine serum albumin (BSA). The cells were then resuspended to Hct 10 in ALP-BSA (BSA 10 mg/ml) buffer. Neutravidin (Pierce catalog #31000) 1 mg/ml solution in ALP-BSA (BSA 10 mg/ml) buffer was added to cells in a 1:10 ratio (i.e., to 500 ul cells, 50 ul neutravidin solution was added). The cells were incubated at room temperature for 30 minutes on a Nutator. The cells were then washed once with ALP-BSA (BSA 1 mg/ml) buffer.

The cells were then resuspended to Hct 10 in ALP-BSA (BSA 1 mg/ml) buffer. Biotinylated paraoxonase was added to cells in a saturating amount (assuming a level of decoration of approximately 20,000/cell). The cells were incubated at room temperature for 30 minutes on a Nutator. The incubated cells were then washed with ALP-BSA (BSA 1 mg/ml) buffer. The number of decorations/cell was determined and cells were prepared for injection.

ii) Injection Protocol

The cells to be injected were prepared in a volume of approximately 10% of the animal's blood volume. In the rats of the present experiment this was calculated as 70 ml blood/kg body weight. The rats were anesthetized using a mixture of ketamine (95 mg/kg) and xylezine (12 mg/kg). A tourniquet was applied to the animal's tail and a catheter was inserted into one of the lateral tail veins. The preparation of decorated cells was injected slowly. Approximately 5 minutes after injection, a blood sample was obtained though a subclavian venipuncture to assess the success of the injection. The animal was allowed to recover prior to challenge.

iii) Results

Dosages of paraoxone were administered i.p. to 170 g Fisher rats. 5X paraoxone (X=published LD50) was uniformly lethal in control rats having no modified red blood cells. In the experimental rat population, the modified red blood cells were fully protective to challenge at 5X (2 out of 2 rats), 7X (3 out of 3 rats) and 10X (2 out of 2 rats) paraoxone.

What is claimed is:

1. A modified red blood cell which is long-lived in circulation, the modified red blood cell bearing on its surface at least one biomolecule capable of neutralizing challenge by a chemical agent.

2. The modified red blood cell of claim 1 wherein the chemical agent exerts a deleterious effect on an organism through molecular interactions within nervous tissue.

3. The modified red blood cell of claim 2 wherein the nerve agent causes death in an individual by inhibiting synaptic acetylcholinesterase.

4. The modified red blood cell of claim 3 wherein the nerve agent is an organophosphorus cholinesterase inhibitor.

5. The modified red blood cell of claim 4 wherein the nerve agent is VX.

6. The modified red blood cell of claim 4 wherein the nerve agent is a G-agent.

7. The modified red blood cell of claim 6 wherein the G-agent is selected from the group consisting of GB, GD and GF.

* * * * *